US00PP17243P2

(12) United States Plant Patent
Trees

(10) Patent No.: US PP17,243 P2
(45) Date of Patent: Nov. 28, 2006

(54) ***ANGELONIA* PLANT NAMED 'BALANGDAROS'**

(50) Latin Name: *Angelonia angustifolia*
Varietal Denomination: Balangdaros

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/270,028

(22) Filed: Nov. 9, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

European Plant Breeders' Rights application No. 2005/2329 filed Nov. 16, 2005.

*Primary Examiner*—Kent Bell
*Assistant Examiner*—Louanne Krawczewicz Myers
(74) *Attorney, Agent, or Firm*—Audrey Charles

(57) ABSTRACT

A new and distinct cultivar of *Angelonia* plant named 'Balangdaros' characterized by its rose-pink colored flowers with darker pink spots, medium-sized flowers, and moderately vigorous, upright growth habit.

1 Drawing Sheet

Latin name of genus and species of plant claimed: *Angelonia angustifolia.*
Variety denomination: 'Balangdaros'.

BACKGROUND OF THE INVENTION

The present invention relates to a new and distinct cultivar of *Angelonia* plant botanically known as *Angelonia angustifolia* and hereinafter referred to by the cultivar name 'Balangdaros'.

The new cultivar was developed by the inventor in a controlled breeding program during January 2003 at Arroyo Grande, Calif. The objective of the breeding program was the development of *Angelonia* cultivars with unique flower colors, continuous flowering and moderately vigorous, freely branching and upright, growth habit.

The female (seed) parent of the new cultivar was the proprietary *Angelonia angustifolia* breeding selection designated BFP-895, not patented, characterized by its large dark purple-colored flowers, dark green-colored foliage, medium vigor, and upright growth habit. The male (pollen) parent of the new cultivar was the proprietary *Angelonia angustifolia* breeding selection designated BFP-873, not patented, characterized by its dark purple-colored flowers, dark green-colored foliage, medium vigor, and upright growth habit. The new cultivar was discovered and selected by the inventor as a single flowering plant within the progeny of the above stated cross-pollination on September 2003 in a controlled environment at Arroyo Grande, Calif.

Asexual reproduction of the new cultivar by terminal stem cuttings since September 2003 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balangdaros' as a new and distinct cultivar of *Angelonia* plant:

1. Rose-pink colored flowers with darker pink spots;
2. Medium-sized flowers; and
3. Moderately vigorous, upright growth habit.

Plants of the new cultivar differ from plants of the female parent primarily in flower color and from plants of the male parent primarily in flower color.

Of the *Angelonia* cultivars known to the inventor, the most similar to 'Balangdaros' is the *Angelonia* cultivar 'Balangroki', not patented. However, in side-by-side comparisons, plants of the new cultivar differ from plants of 'Balangroki' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangdaros'. The plants were grown in 10 cm pots for 11 weeks in a greenhouse at West Chicago, Ill.

DETAILED BOTANICAL DESCRIPTION

Figure 1:
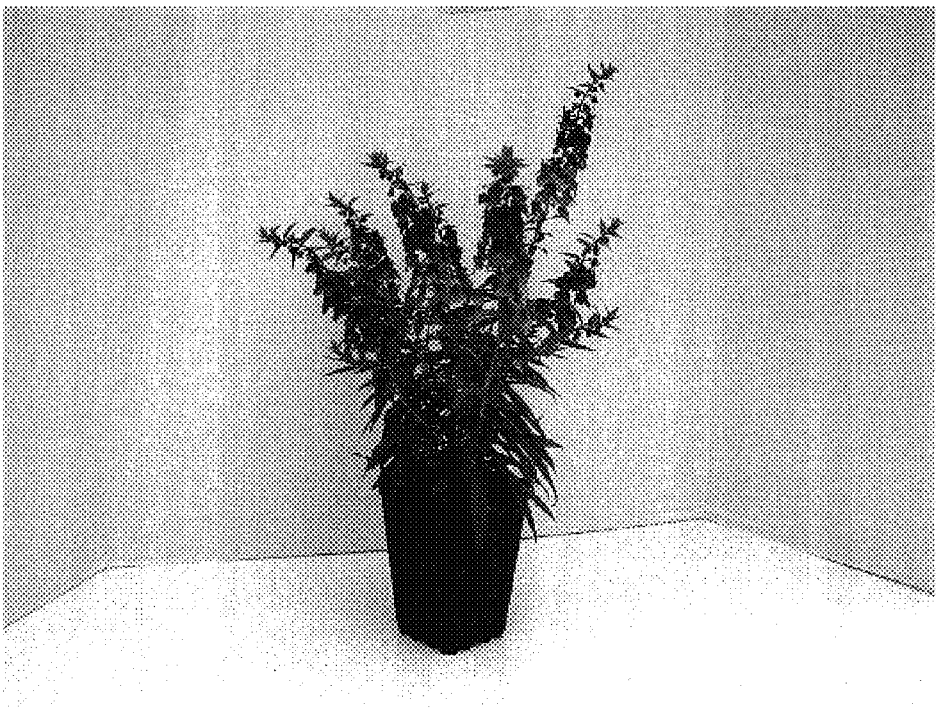
FIG. 1 illustrates a side view of the overall growth and flowering habit of 'Balangdaros'.
Figure 2:
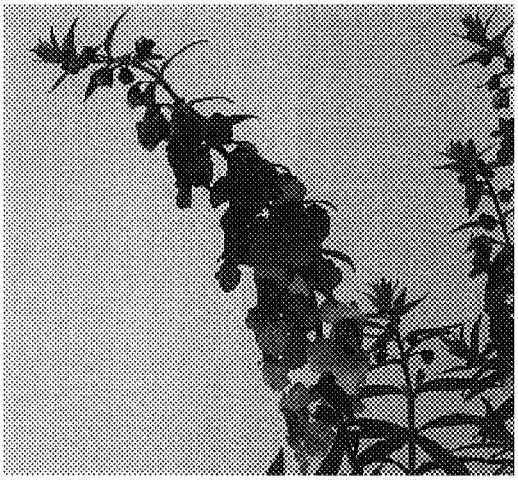
FIG. 2 illustrates a close-up view of the inflorescence of 'Balangdaros'.
Figure 3:
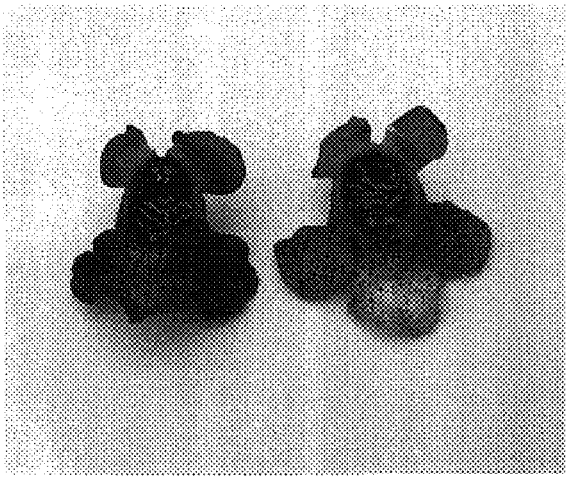
FIG. 3 illustrates a close-up view of the individual flowers of 'Balangdaros' showing variation in color from first open on left to fully mature on right.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Apr. 13, 2005. The readings were taken between 1:00 p.m. and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 11 weeks while utilizing a soilless growth medium. Greenhouse temperatures were maintained at approximately 75° F. to 85° F. (24° C. to 29° C.) during the day and approximately 62° F. to 70° F. (17° C. to 21° C.) during the night. Greenhouse light levels were maintained at approximately 6,000 to 10,000 footcandles during the day.

Botanical classification: *Angelonia angustifolia*, cultivar Balangdaros.

Parentage:

*Female (seed) parent.*—Proprietary *Angelonia angustifolia* breeding selection designated BFP-895, not patented.

*Male (pollen) parent.*—Proprietary *Angelonia angustifolia* breeding selection BFP-873, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous.

*Form.*—Upright, freely branching.

*Size.*—Height (from soil level to top of plant plane): Approximately 25.9 cm. Diameter (area of spread): Approximately 25.3 cm.

*Main branch.*—Quantity per plant: Approximately 4. Shape: Square in cross section. Strength: Strong. Length from soil level to base of raceme: Approximately 29.0 cm. Diameter: Approximately 3.7 mm. Texture: Glabrous. Color: 145B. Internode length at center of branch: Approximately 1.6 cm.

*Foliage.*—Quantity of leaves per main branch: Approximately 14. Type: Simple. Fragrance: None. Arrangement: Opposite. Orientation to stem: Obtuse. Shape: Elliptic. Margin: Serrate. Apex: Acuminate. Base: Sessile. Length of leaf at center of branch: Approximately 6.6 cm. Width of leaf at center of branch: Approximately 1.2 cm. Texture of upper and lower surfaces: Glabrous. Venation pattern: Pinnate. Color of upper surface of young and mature foliage: Slightly darker than 137A with venation of 144C. Color of lower surface of young and mature foliage: 137C with venation of 144D.

Flowering description:

*Flowering habit.*—'Balangdaros' is freely flowering under outdoor growing conditions with substantially continuous blooming from spring through autumn and year round in greenhouse environment.

*Time to first flower.*—Approximately 13 weeks from sticking of unrooted cutting.

*Lastingness of individual bloom on the plant.*—Approximately 7 to 10 days.

*Inflorescence type/description.*—Terminal racemes. Length: Approximately 12.6 cm. Width: Approximately 4.3 cm. Number per plant: Approximately 2 open racemes per plant at 11 weeks. Number of fully open flowers per raceme at any one time: Approximately 15.

Flower description:

*Type/fragrance.*—Bilabiate. Very slight, sweet fragrance.

*Bud.*—Rate of opening: 3 to 4 days from first color to fully open. Shape: Globular. Length: Approximately 8.2 mm. Diameter: Approximately 6.5 mm. Color of upper surface: 150D with 73A at base. Color of lower surface: 150C with spots of 77A.

*Flower size/aspect.*—Length: Approximately 2.2 cm. Width: Approximately 1.8 cm. Depth: Approximately 7.0 mm. Aspect: Facing outward.

*Petals.*—Quantity: 5 per flower, fused at base forming a throat, an upper lip with two petals, and a lower lip with three petals — one central and one lateral on each side. Petal shape of upper lip and lower lip petals: Obovate.

*Upper lip.*—Petal apex: Emarginate. Petal margin: Entire, undulate. Length of petals from throat: Approximately 6.4 mm. Width of each petal: Approximately 8.7 mm. Color of upper surface: 72B. Color of lower surface: 72C. Texture of upper surface: Densely glandular-pubescent. Texture of lower surface: Glabrous.

*Lower lip, lateral petals.*—Petal apex: Emarginate. Petal margin: Entire, undulate. Length of petals from throat: Approximately 7.4 mm. Width of each petal: Approximately 8.4 mm. Color of upper surface: 72B with spots of N79C. Color of lower surface: 72B with streaks of 75D. Texture of upper surface of petals: Densely glandular-pubescent. Texture of lower surface of petals: Densely pubescent with very short glandular hairs.

*Lower lip, central petal.*—Petal apex: Emarginate. Petal margin: Entire, undulate. Length of petal from palate: Approximately 7.6 mm. Width of petal: Approximately 8.6 mm. Color of upper surface: N155B with spots of 77A. Color of lower surface: N155B with N72B along margin. Texture of upper surface of petals: Densely glandular-pubescent. Texture of lower surface of petals: Densely pubescent with very short glandular hairs. Gland color: Colorless, translucent.

*Throat.*—Length: Approximately 5.7 mm. Width: Approximately 6.0 mm. Texture of inner and outer surfaces: Glabrous. Color of inner and outer surfaces: N155B with spots and streaks of 83A. Palate color: N155B with spots of 77A. Palate texture: Glabrous, pubescent along margin. Teeth color: N155B with spots of 83A.

*Pedicel.*—Strength: Good. Length: Approximately 7.6 mm. Diameter: Approximately 0.5 mm. Angle to stem: Acute. Texture: Glabrous. Color: N144B with overlay of N187A.

*Calyx.*—Shape: Five-pointed star, cupped. Width: Approximately 5.0 mm.

*Sepal.*—Quantity per flower: 5. Shape: Lanceolate. Margin: Entire. Base: Fused. Apex: Acuminate.

Length: Approximately 3.9 mm. Width: Approximately 1.7 mm. Texture of upper or inner surface: Glabrous. Texture of lower or outer surface: Puberulent. Color of upper and lower surfaces: 143A.

*Reproductive organs.*—Androecium: Stamen quantity: 4 per flower. Stamen length: Approximately 4.0 mm. Filament color: Lighter than N155B. Anther shape: Bilobed. Anther length: Approximately 1.8 mm. Anther color: N80C. Amount of pollen: Moderate. Pollen color: 155D. Gynoecium: Pistil quantity: One per flower. Pistil length: Approximately 4.0 mm. Stigma length: Approximately 0.7 mm. Stigma color: 150D. Style length: Approximately 2.0 mm. Style color: 155C. Ovary diameter: Approximately 1.3 mm. Ovary texture: Puberulent. Ovary color: 145B.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangdaros', substantially as herein shown and described.

* * * * *